United States Patent
Medoff

(10) Patent No.: US 10,357,294 B2
(45) Date of Patent: Jul. 23, 2019

(54) METHOD OF SECURING A PLATE TO A BONE AT A FRACTURE SITE UTILIZING A DETACHABLE INSERTER

(71) Applicant: TriMed, Incorporated, Santa Clarita, CA (US)

(72) Inventor: Robert Medoff, Kailua, HI (US)

(73) Assignee: TriMed, Incorporated, Santa Clarita, CA (US)

( * ) Notice: Subject to any disclaimer, the term of this patent is extended or adjusted under 35 U.S.C. 154(b) by 248 days.

(21) Appl. No.: 15/194,953

(22) Filed: Jun. 28, 2016

(65) Prior Publication Data

US 2017/0000534 A1    Jan. 5, 2017

Related U.S. Application Data

(60) Provisional application No. 62/187,545, filed on Jul. 1, 2015.

(51) Int. Cl.
*A61B 17/80* (2006.01)
*A61B 17/00* (2006.01)
*A61B 17/32* (2006.01)

(52) U.S. Cl.
CPC ............ *A61B 17/808* (2013.01); *A61B 17/80* (2013.01); *A61B 2017/0046* (2013.01); *A61B 2017/00424* (2013.01); *A61B 2017/00469* (2013.01); *A61B 2017/320044* (2013.01); *A61B 2017/320056* (2013.01)

(58) Field of Classification Search
CPC .............................. A61B 17/80; A61B 17/808
See application file for complete search history.

(56) References Cited

U.S. PATENT DOCUMENTS

| 6,916,323 B2* | 7/2005 | Kitchens | A61B 17/1725 |
| | | | 606/104 |
| 7,819,877 B2* | 10/2010 | Guzman | A61B 17/1635 |
| | | | 606/86 B |
| 8,231,627 B2* | 7/2012 | Huebner | A61B 17/1684 |
| | | | 606/280 |
| 9,044,344 B2* | 6/2015 | Nelson | A61F 2/4612 |
| 9,861,407 B2* | 1/2018 | Early | A61B 17/80 |

OTHER PUBLICATIONS

Skeletal Dynamics Geminus Dorsal Spanning Plate Surgical Technique Guide MKT-00060-00RAB.†

\* cited by examiner
† cited by third party

*Primary Examiner* — Nicholas W Woodall
(74) *Attorney, Agent, or Firm* — Wood, Phillips, Katz, Clark & Mortimer

(57) ABSTRACT

The combination of a plate and inserter for the plate. The plate is configured to be operatively placed at a bone fracture site and secured with at least one fastener to stabilize bone portions between which a fracture is located. Structure cooperating between the plate and inserter is configured to releasably maintain the plate operatively engaged with the inserter. The operatively engaged plate is movable together with the inserter whereby a user can manipulate the operatively engaged plate through the inserter. The plate has a leading end with a tapered configuration to facilitate dissection of soft tissue from a bone surface to allow a surface on the plate that trails the advancing leading end to be operatively placed against the bone surface across the bone fracture site.

30 Claims, 10 Drawing Sheets

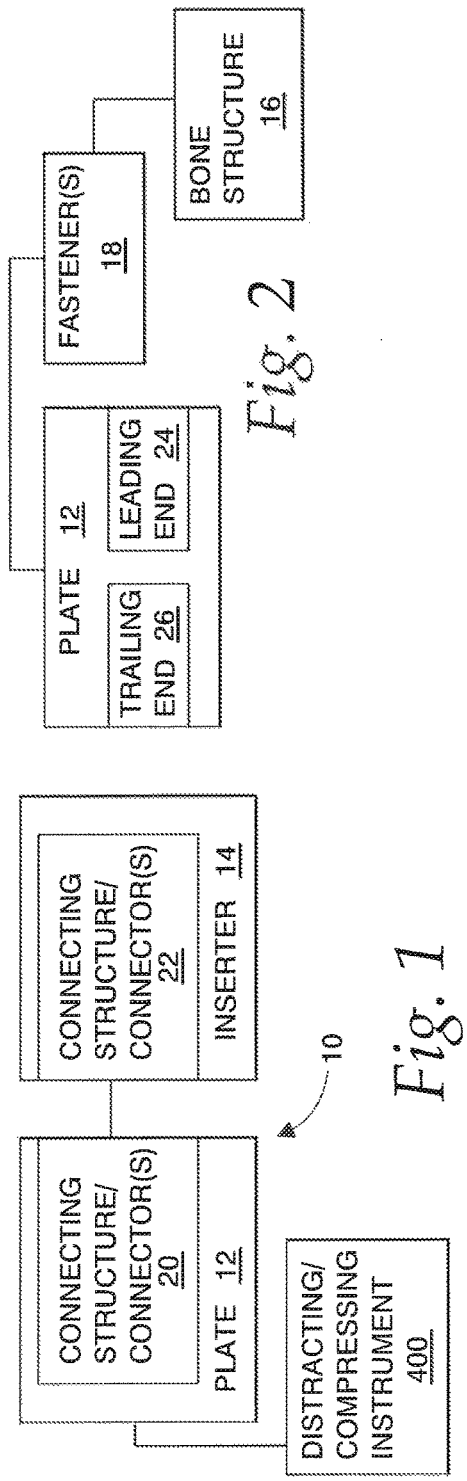
Fig. 1
Fig. 2
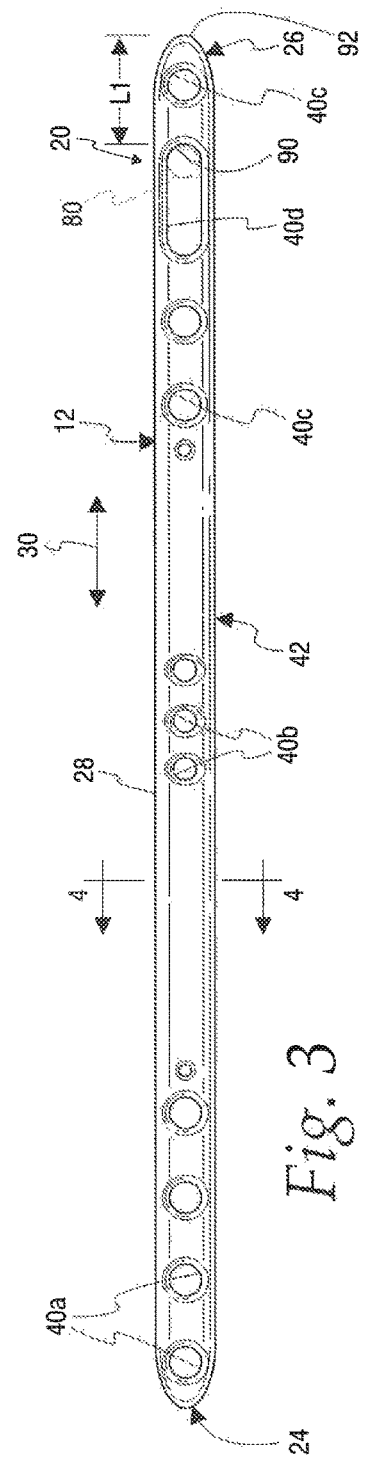
Fig. 3

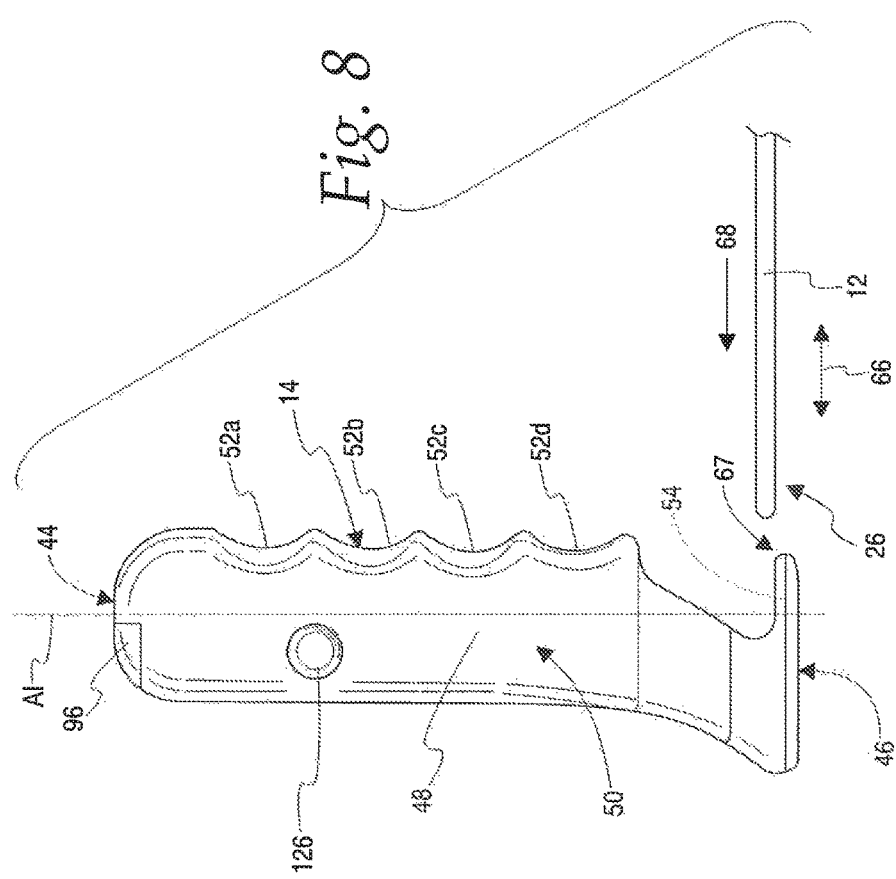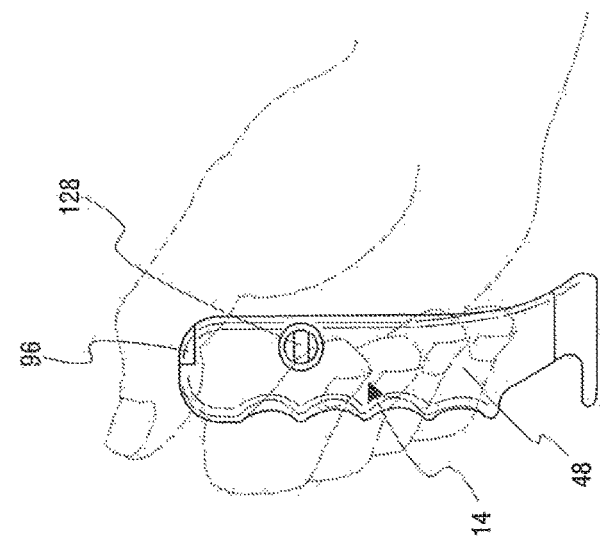

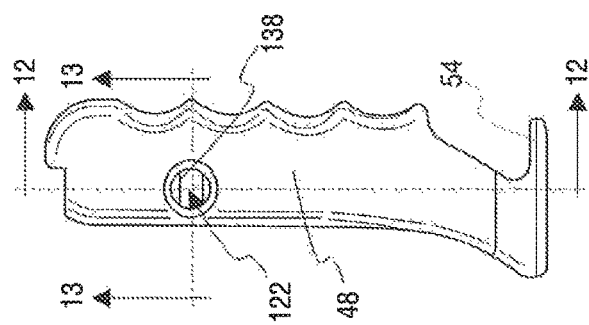
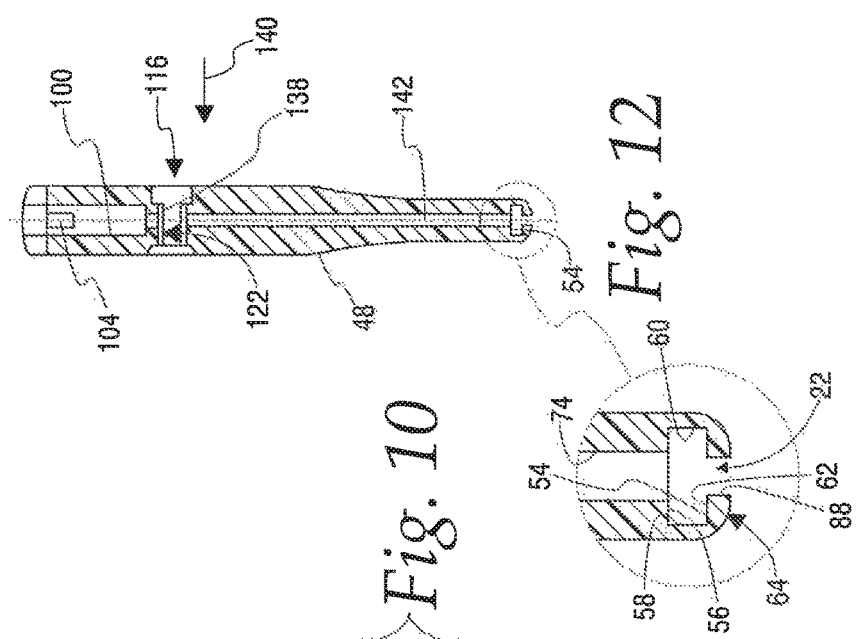
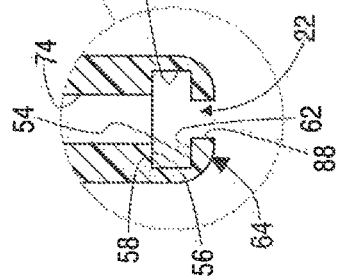
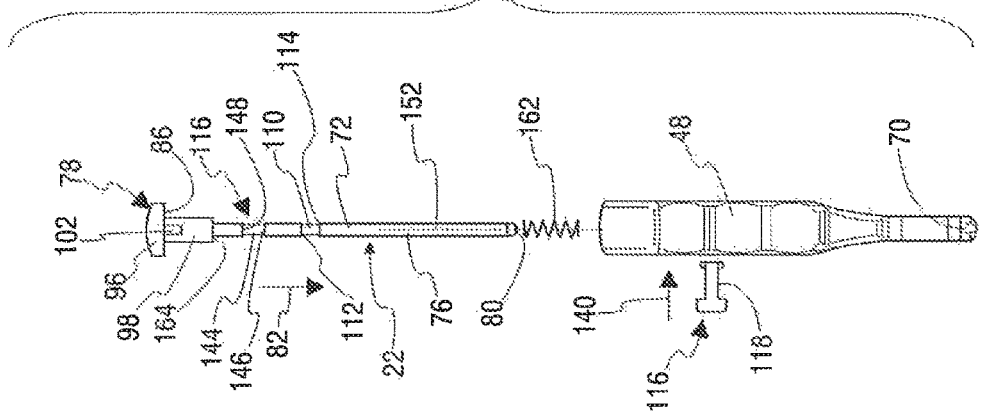

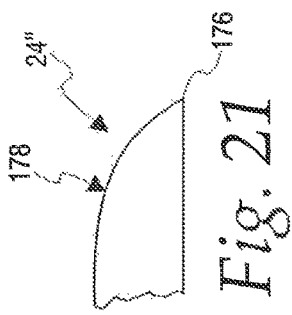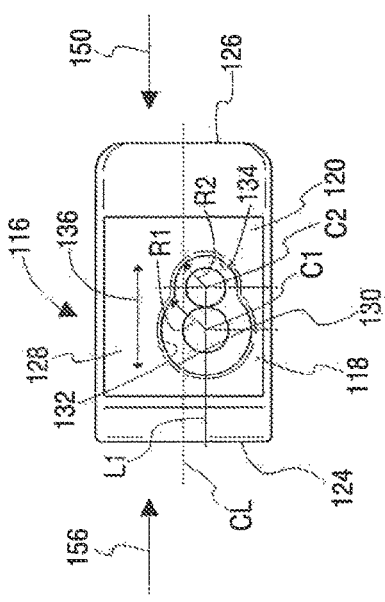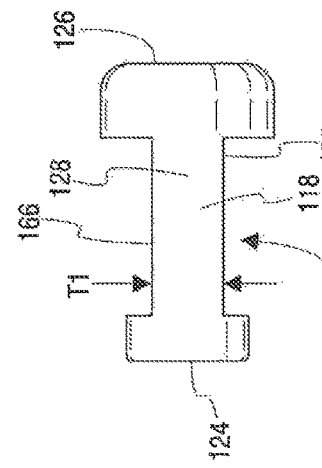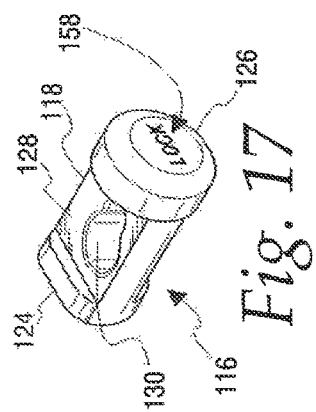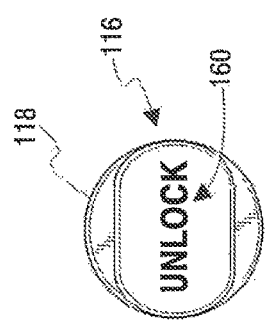

METHOD OF SECURING A PLATE TO A BONE AT A FRACTURE SITE UTILIZING A DETACHABLE INSERTER

CROSS-REFERENCE TO RELATED APPLICATIONS

This is a non-provisional application claiming priority to U.S. Provisional Ser. No. 62/187,545, filed Jul. 1, 2015, entitled "Method of Securing a Plate to a Bone at a Fracture Site Utilizing a Detachable Inserter", which is hereby incorporated by reference in its entirety.

BACKGROUND OF THE INVENTION

Field of the Invention

This invention relates to bone fractures and, more particularly, to a plate and inserter combination that can be used to operatively place and secure the plate at a desired location at a fracture.

Background Art

Minimal insertion surgery, or MIS, is a technique in which a plate is inserted along the surface of a bone through a small incision. The surgeon first makes a limited incision and dissects down to the bone surface, and then uses an instrument to dissect through soft tissues for a distance far enough to produce a channel to accept the plate length desired. Once this is done, a plate is applied through the limited incision and fixed with fasteners placed percutaneously through the plate holes. The plate serves to stabilize the bone on each side of the fracture, to minimize motion between the bone ends to promote healing. In addition, often the plate functions to hold ends to promote healing. In addition, often the plate functions to hold opposing bone ends apart, thereby preventing shortening of the bone. Structural rigidity of the construct is improved if the plate is close to or at the bone surface.

Consequently, multiple steps must be serially performed with multiple instruments to complete the plate placement and its securement. The size of the instrument used to create the soft tissue channel may not be the same as the size of the plate that is inserted; this can create difficulties with passage of the plate. Furthermore, since the dissecting instrument needs to be removed prior to introduction of the plate, soft tissues may drop into the path created by the instrument, further obstructing placement of the plate or causing the plate to be guided in a different path than intended. Passage of the plate into correct position may also be awkward since the surgeon is required to hold the end of the plate with his/her fingers and push in lengthwise, or try to hold the end of the plate with a clamp to control the plate during insertion. In the latter situation, the clamp may not securely hold the plate, causing it to uncouple or misdirect the orientation. Because of this potential, the clamp is generally held in place with sufficient force that it may scratch or damage the surface of the plate/implant. Further, the initial incision has to be made large enough that the plate insertion can be readily carried out without significant interference from tissue at the site.

SUMMARY OF THE INVENTION

In one form, the invention is directed to the combination of: a) a plate configured to be operatively placed at a bone fracture site and secured with at least one fastener to stabilize bone portions between which a fracture is located, the plate having a tapered leading end; and b) an inserter. Structure cooperating between the plate and inserter is configured to releasably maintain the plate operatively engaged with the inserter. The operatively engaged plate is movable together with the inserter whereby a user can reorient and advance the operatively engaged plate through the inserter. With the plate operatively engaged with the inserter, the plate and inserter are configured so that by manipulating the inserter the tapered leading end can be advanced to dissect soft tissue along a bone surface to allow a surface portion on the plate that trails the advancing leading end to be operatively placed against the bone surface across the bone fracture site.

In one form, the inserter is configured to be changed between a first state, wherein the plate may translate in at least one line to be selectively: a) operatively positioned in a receptacle on the inserter; and b) separated from the inserter, and a second state wherein the operatively positioned plate is engaged/coupled with the inserter.

In one form, the inserter has a top and bottom and a body that has a vertically elongate shape with an exterior surface configured to be grasped between a user's palm and a plurality of a user's fingers.

In one form, the vertically elongate shape has an axis. The plate has a lengthwise axis. The axis of the vertically elongate shape is at an angle of at least 45 degrees to the lengthwise axis of the plate with the plate operatively engaged with the inserter.

In one form, the body has a plurality of vertically spaced, discrete receptacles each for a user's finger.

The structure cooperating between the plate and inserter includes a slot on the body in which a part of the plate resides with the plate operatively engaged.

In one form, the body and the part of the plate are configured so that the part of the plate is movable into and out of the slot by relatively translating the body and the part of the plate along a first line.

In one form, the first line is horizontally oriented relative to the body.

In one form, the structure cooperating between the plate and inserter has a fixing component that is movable guidingly relative to the body between engaged and released positions. The plate part is movable into and out of the slot with the fixing component in the released position and maintained in the slot with the fixing component in the engaged position.

In one form, the body and the part of the plate are configured so that the part of the plate is movable into and out of the slot by relatively translating the body and the part of the plate along a first line. The fixing component is movable between the engaged and released positions along a second line that is transverse to the first line.

In one form, the plate has an opening. The fixing component has a free end that extends into the opening with the fixing component in the engaged position.

In one form, the opening is configured to accept a fastener configured to be directed through the opening and into a bone to secure the operatively placed plate.

In one form, the fixing component is normally biased towards the released position.

In one form, the combination further includes a locking assembly having locked and unlocked states. The locking assembly is configured so that in the locked state the fixing component is maintained in the engaged position. The locking assembly is configured so that in the unlocked state the fixing component can move between the engaged and released positions.

In one form, the locking assembly has a block that is movable guidingly relative to the body between first and second positions. The locking assembly is in the locked state with the block in the first position. The locking assembly is in the unlocked state with the block in the second position.

In one form, the block is movable in a substantially straight line between the first and second positions. The body has oppositely facing first and second surfaces. The locking assembly has first and second actuators, respectively at the first and second surfaces, that are engageable by a user to selectively move the block between the first and second positions.

In one form, the combination is provided together with a plurality of fasteners configured to fix the plate to bone at the bone fracture site.

In one form, the plate has an elongate body with a length and a thickness between first and second oppositely facing surfaces. The surface portion on the plate that trails the advancing leading end is a part of one of the first and second oppositely facing surfaces. The surface portion on the plate that trails the advancing leading end is a part of the one of the first and second oppositely facing surfaces. The plate has a plurality of fastener openings each extending through the body and the first and second surfaces.

In one form, the first and second surfaces are substantially flat over a substantial length of the plate body to reside in first and second substantially parallel planes.

In one form, a length of one of the first and second surfaces is twisted out of the first plane to conform to bone at a human ankle region.

In one form, the plate body has a truncated tubular shape over a substantial length of the plate body.

In one form, the leading end of the plate has a dissecting edge and tapers away from the dissecting edge towards a trailing end of the plate to facilitate tissue dissection as the plate is advanced, leading end first, to be operatively placed at the bone fracture site.

In one form, the dissecting edge is situated on a deep surface of the plate. The taper is located at a superficial surface of the plate so as to facilitate dissection in a plane between the bone surface and overlying soft tissue and apposition of the deep surface directly against the bone surface as the leading end is advanced through manipulation of the inserter.

In one form, the leading end has a curved, convex shape as viewed orthogonally to the plane between the bone surface and overlying soft tissue.

In one form, the invention is directed to a method of securing a plate to a bone at a fracture site. The method includes the steps of: obtaining the combination described above; with the plate operatively engaged with the inserter, manipulating the inserter to: a) cause the plate to dissect tissue at the fracture site; and b) operatively place the plate at a desired location at the fracture site; separating the inserter from the plate; and securing the operatively placed plate to bone at the fracture site.

BRIEF DESCRIPTION OF THE DRAWINGS

FIG. 1 is a schematic representation of a system, according to the present invention, for securing a plate to a bone at a fracture site and made up of the combination of a plate and an inserter for the plate;

FIG. 2 is a schematic representation of a plate, as shown in FIG. 1, together with fasteners for securing the plate to a bone structure;

FIG. 3 is a plan view of one exemplary form of plate as shown in FIGS. 1 and 2;

FIG. 4*a* is a view as in FIG. 4 showing an alternative cross-sectional plate shape, according to the invention;

FIG. 5*a* is a perspective view of the plate in FIG. 5 fixed at a patient's ankle region;

FIG. 8 is a side elevation view of the inserter in FIGS. 6 and 7 with the plate separated therefrom;

FIG. 9 is a reduced, elevation view of the inserter from the side opposite that in FIG. 8 and being grasped by a hand for use;

FIG. 10 is an exploded, elevation view of the inserter in FIGS. 6-9;

FIG. 11 is a view, as in FIG. 8, of a body that makes up part of the inserter in FIGS. 6-10;

FIG. 12 is a cross-sectional view of the inserter body taken along line 12-12 of FIG. 11;

FIG. 17 is an enlarged, perspective view of a block making up part of a locking assembly on the inventive inserter;

FIG. 18 is a plan view of the block in FIG. 17;

FIG. 19 is an end elevation view of the block in FIGS. 17 and 18;

FIG. 20 is a side elevation view of the block in FIGS. 17-19;

FIG. 21 is an enlarged, fragmentary, elevation view of a leading end on a plate that can be used with the inventive inserter;

DETAILED DESCRIPTION OF THE PREFERRED EMBODIMENT

Figure 4:
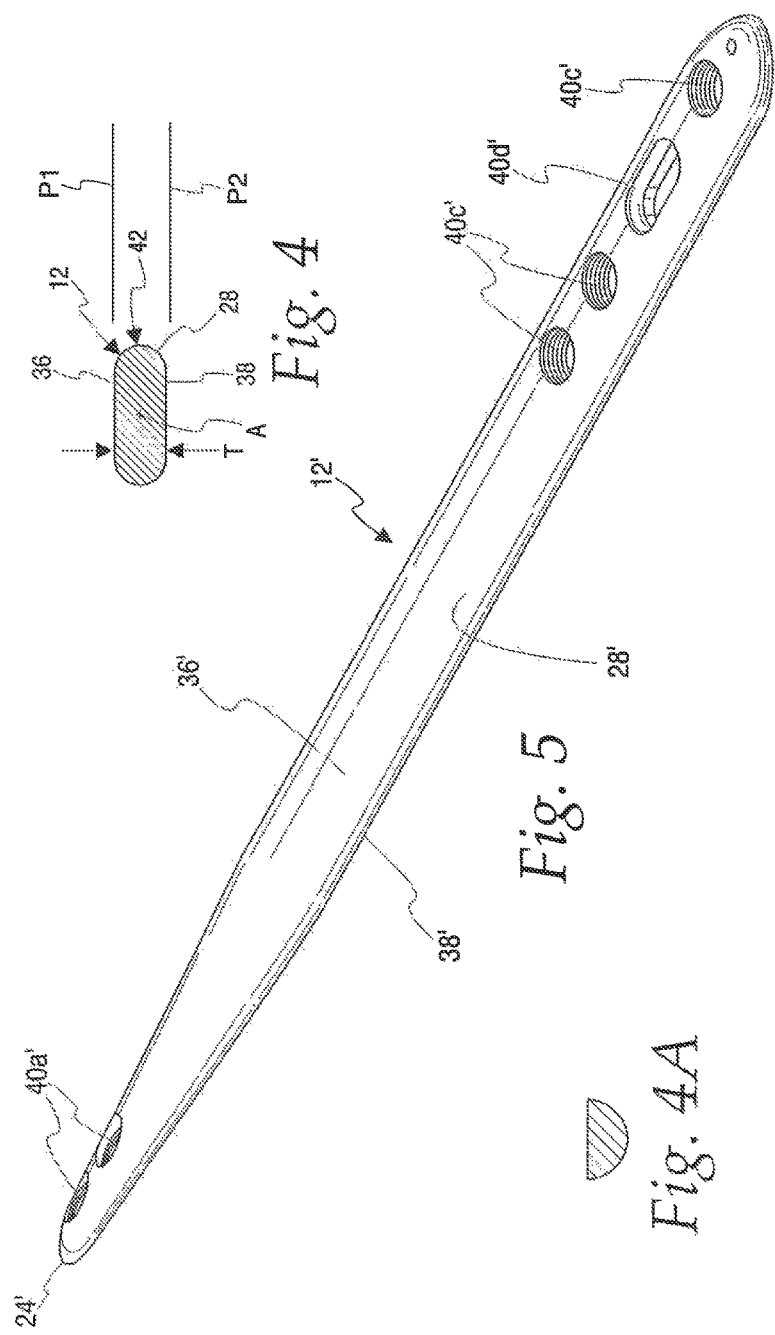
FIG. 4 is a cross-sectional view of the plate taken along line 4-4 of FIG. 3.

In its basic form, the invention is directed to a system, shown schematically at 10 in FIG. 1, consisting of the combination of a plate 12 and an inserter 14 for the plate 12.

The plate 12 is configured to be operatively placed with respect to bone structure 16 at a fracture site, as shown additionally in FIG. 2, also in schematic form. Plate securement is effected through at least one fastener 18. Through this arrangement, bone portions can be stabilized by the secured plate 12 that bridges a fracture.

Cooperating connecting structure 20, 22 is provided respectively on the plate 12 and inserter 14. Each of the connecting structures 20, 22 may be in the form of one or more connectors. The connecting structure 20, 22 is configured to allow the plate 12 to be releasably maintained operatively engaged with the inserter 14.

The operatively engaged plate 12 is movable together with the inserter 14, whereby a user can reorient and advance the operatively engaged plate 12 through the inserter 14 to conveniently effect its placement at a fracture site.

The plate 12 has a leading end 24 and a trailing end 26. The leading end 24 has a tapered configuration to facilitate direction of the leading end 24 past tissue as the inserter 14 is manipulated to cause the plate 12 to be operatively placed at a bone fracture site.

With the plate 12 operatively engaged with the inserter 14, the plate 12 and inserter 14 are configured so that by manipulating the inserter 14, the tapered leading end 24 can be advanced to dissect soft tissue along a bone surface to allow a surface portion in the plate, that trails the advancing leading end 24, to be operatively placed against the bone surface across the bone fracture site.

The schematic showing of the components in FIGS. 1 and 2 is intended to encompass virtually an unlimited number of variations of those components in the preferred embodiments, described hereinbelow. The schematic showing is intended to encompass all such variations as well as different interactions thereof, which would be obvious to one skilled in the art with the teachings of the invention in hand.

For example, the invention contemplates that the leading end 24, as shown in FIG. 2, have a contour that avoids hanging up on tissue as the leading end is advanced through and past tissue in the vicinity of a fracture site. One specific and preferred configuration for the leading end 24 will be described hereinbelow, but this should be viewed as exemplary in nature only. Further, the bone structure 16 is not limited to any particular anatomical site. Exemplary plate configurations are disclosed hereinbelow that are particularly adaptable to fixation of bone portions in the wrist and ankle regions.

One exemplary form of the plate 12 is shown in FIGS. 3 and 4. The plate 12 has an elongate body 28 with a length, as indicated by the double-headed arrow 30, between the leading and trailing ends 24, 26, respectively, and a lengthwise axis A. The body 28 has a thickness T between first and second oppositely facing surfaces 36, 38, respectively. As depicted, the surfaces 36, 38 may be substantially flat and parallel to each other over substantially the entire length of the body 28 between the leading and trailing ends 24, 26, to thereby reside in spaced parallel planes P1, P2. Alternatively, one of these surfaces may be curved, as with the body having a truncated tubular cross-sectional contour, as shown in FIG. 4a, for additional plate stiffness and resistance to bending.

The body 28 has a plurality of fastener openings 40a, 40b, 40c each extending through the body 28 and the first and second surfaces 36, 38. An opening 40d may be configured to accept a fastener 18 or, alternatively, may be used only as part of the connecting structure 20, as described below. The openings 40 and the particular fasteners 18 used therein are generally conventional in nature. The fastener openings 40b are shown with bearings to allow a surgeon the option of placing polyaxial locking fasteners therein to support a fractured joint surface.

The perimeter body edge 42 is rounded, including at the leading and trailing ends 24, 26, to facilitate guided advancement through and against tissue and to avoid the presence of any sharp edges that might cut or irritate tissue. As seen from the FIG. 3 perspective, the leading end 24 has a curved, convex shape.

As depicted, this plate 12 is adaptable conveniently, but not exclusively, for use at a wrist region. The configuration shown can span an extremely complex distal radius fracture and, as explained below, permits potentially rapid stabilization thereof, as when other injuries to the patient make take precedence and the surgeon does not have the luxury of spending the necessary time to effect a permanent repair. However, the plate 12 can be permanently inserted and secured, where it is operatively placed, through the appropriate fasteners 18.

Figure 5:
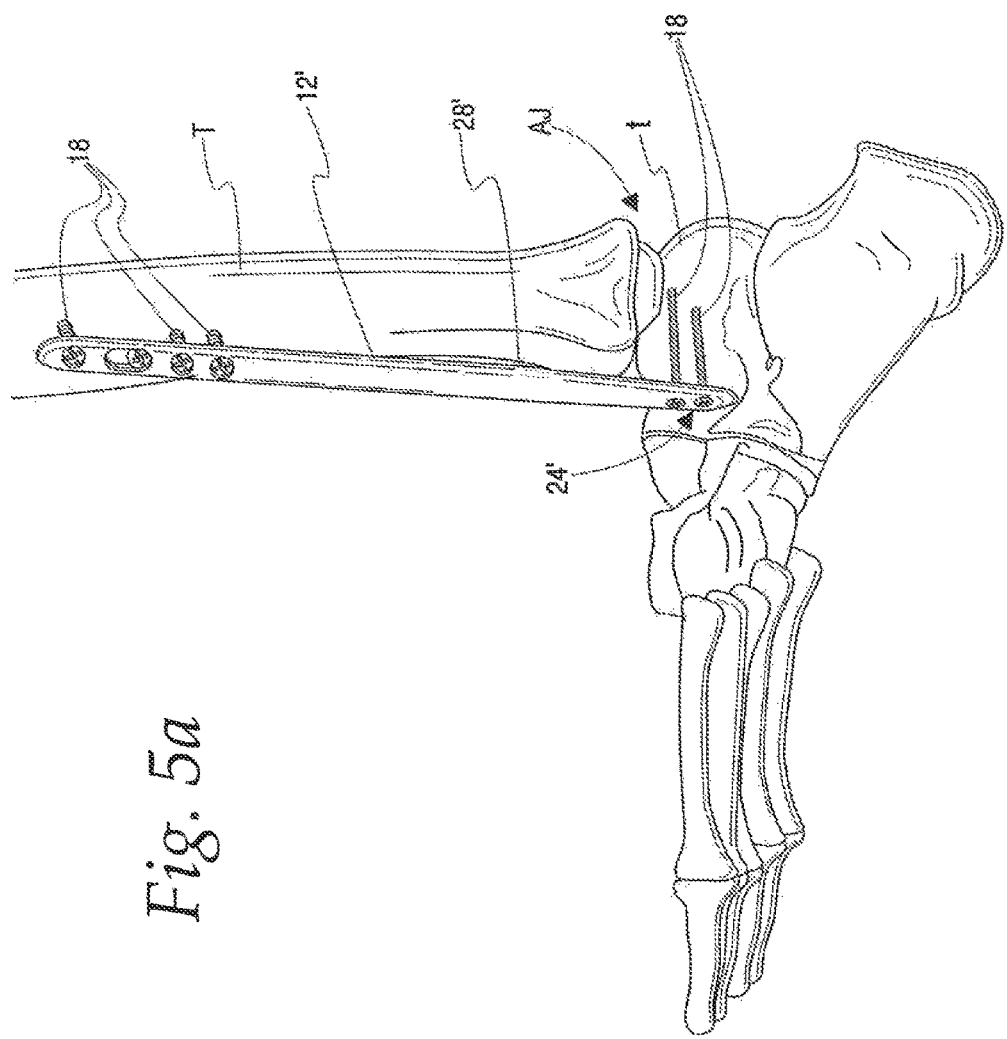
FIG. 5 is a perspective view of a modified form of plate within the schematic showing in FIGS. 1 and 2.
Figure 6:
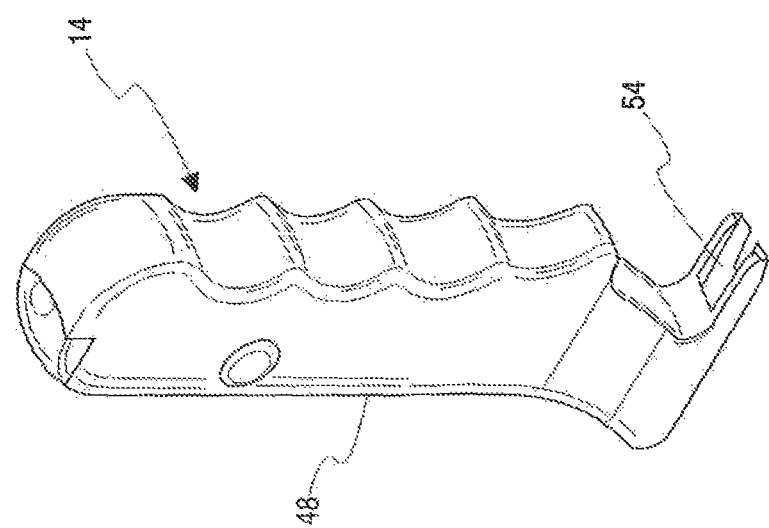
FIG. 6 is a perspective view of one exemplary form of inserter, as shown in FIGS. 1 and 2, in combination with the plate in FIGS. 3 and 4.
Figure 7:
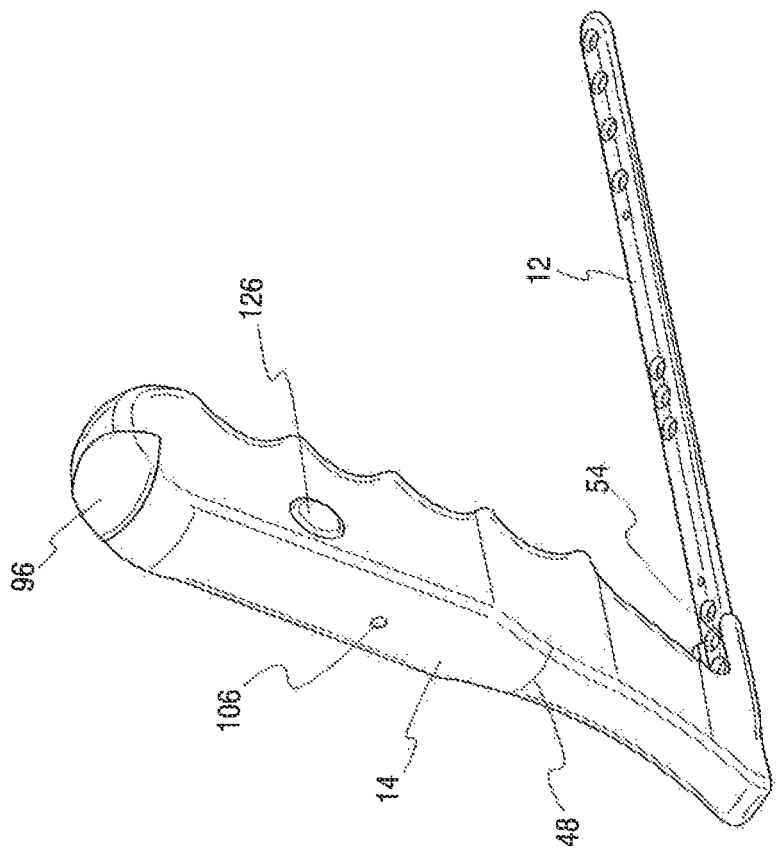
FIG. 7 is a view of the inserter in FIG. 6 from a different perspective and without the plate.

In FIG. 5, a modified form of plate, according to the invention, is shown at 12'. The plate 12' has a body 28' with a configuration generally the same as that of the body 28. Whereas the first and second surfaces 36, 38 on the plate 12 respectively reside in parallel planes P1, P2 over substantially the entire length of the body 28, on the plate 12' at least a portion of the corresponding second surface 38', that engages the bone, is formed/twisted to conform to a non-flat contour. The first surface 36' may have a conforming shape, but this is not required. This particular configuration is suitable for complex fractures of the lower tibia/ankle, as described below.

While usable as a permanent structure, the plate 12' is usable alternatively to temporarily stabilize the lower extremity, as until swelling subsides and the patient is stabilized to allow a more definitive surgery to be performed. As depicted, the plate 12' is designed for the antero-lateral side of the lower tibia T and spans the ankle joint as shown in FIG. 5a. The leading end 24', which is the lower end of the implanted plate 12', has fastener openings 40a', formed as threaded openings that diverge in two directions to allow placement of a locking screw into the talus t, which is at the distal side of the ankle joint at AJ. The surgeon can insert the plate 12' through a small incision at the anterolateral tibia and tunnel the plate 12' distally to the anterolateral portion of the ankle. The plate body 28' can then be secured distally using the fasteners 18 in the openings 40a' and proximally through threaded fastener openings 40c' (and potentially 40d'), which also anchor in the tibia.

One exemplary form of inserter 14 will now be described with respect to FIGS. 6-20. The inserter 14 may be used with either plate 12, 12', or another plate configuration.

The inserter 14 has a top and bottom, respectively identified at 44 and 46. The inserter 14 has a body 48 with a vertically elongate shape with an exposed, exterior surface 50 and a vertical axis A1. The body 48 is configured to be grasped between a user's palm and a plurality of a user's fingers by wrapping the hand around the body 48 generally as one would grasp the back handle on a wood planer, or the like, as shown in FIG. 9. The orientation of the length of the handle along the axis A1, that is generally perpendicular to the axis A of the operatively positioned plate, allows both considerable power to be applied by the surgeon's arm while the plate is inserted, yet still provides fine, precise control of the direction of the tip of the plate as it is inserted through the soft tissues. The angle between the A1, A2 with the plate operatively positioned while shown to be approximately 90°, is at least 45°. The body 48 has a plurality of vertically spaced, discrete receptacles 52a, 52b, 52c, 52d, each to accommodate a user's finger.

The connecting structure/connector(s) 22 on the inserter 14 consists of a receptacle, shown in the form of an elongate slot 54 in the body 48 in which a part of the plate 12 resides with the plate 12 operatively positioned and coupled/engaged. The part of the plate 12 is a portion of the plate 12 at the trailing end 26 thereof.

The slot 54 is bounded by: a) an upper, downwardly facing surface 56; b) facing vertically extending surfaces 58, 60; and c) an upwardly facing surface 62 defined by a split bottom wall portion 64 which, among other things, facilitates cleaning. The slot 54 is at least nominally matched in shape to the trailing end 26 of the plate 12 so that the trailing end 26 of the plate 12 is movable into and out of the slot 54 by relatively translating the body 48 and trailing end 26 of the body along a first line, indicated by the double-headed arrow 66 in FIG. 8. In this embodiment, the line is substantially horizontally oriented relative to the body 48.

For the inserter 14 to operatively engage the plate 12, the plate is initially situated as shown in FIG. 8, with the trailing plate end 26 aligned at the entry 67 to the slot 54. The plate 12 is then translated horizontally in the direction of the arrow 68 until the trailing end 26 slides into the slot 54, which movement is eventually arrested by a stop surface 70 on the body 48 at a closed end of the slot 54 at which point the plate 12 is operatively positioned with respect to the inserter 14.

With the trailing end 26 fully seated in the slot 54, this relationship is maintained by additional cooperating connecting structure/connectors 20, 22, as shown schematically in FIG. 1. More specifically, the connecting structure 22 includes an elongate fixing component 72 that is movable guidingly relative to the body 48 in a vertical direction. The body 48 has a stepped diameter vertical through opening 74 that receives the fixing component 72. The fixing component 72 has an elongate, cylindrical body 76 with an enlarged actuating end 78 and a locking end 80.

The fixing component 72 is connected to the body 48 by aligning the locking end 80 with the top of the through opening 74 and advancing the fixing component 72 downwardly, as indicated by the arrow 82 in FIG. 10. This downward movement of the fixing component 72 is arrested by an upwardly facing surface 84 at the top of the body 48 that abuts to an oppositely facing surface 86 on the actuating end 78 of the fixing component 72. This represents the engaged position for the fixing component 72 wherein the locking end 80 extends through the slot 54, as shown in dotted lines in FIG. 16. The split bottom wall portion 64 defines an opening 88 to accommodate the locking end 80.

With the fixing component 72 in this position, the locking end 80 nests in the plate opening 40d, as shown in FIG. 3, which makes up part of the connecting structure 20. The locking end 80 abuts an edge 90 at the trailing end 90 of the opening 40d such that the plate length L1, between the trailing end of the opening 40d and the extremity 92 of the plate 12 at its trailing end 26, is captive between the locking end 80 and the stop surface 70 on the inserter body.

In this position, the actuating end 78 of the fixing component 72 nests in a complementarily-shaped receptacle/void 94 formed at the top of the body 48. That portion of the actuating end 78 that nests consists of a head 96 beneath which there is an enlarged diameter portion 98 of the body 76 that fits into a complementary seat 100 making up part of the through opening 74. A boss 102 is integrally formed with the enlarged diameter portion 98 and fits in a keyway 104 to facilitate angular alignment of the fixing component 72 and inserter body 48 during assembly and prevent turning of the enlarged diameter portion 98 within the seat 100.

Figure 16:
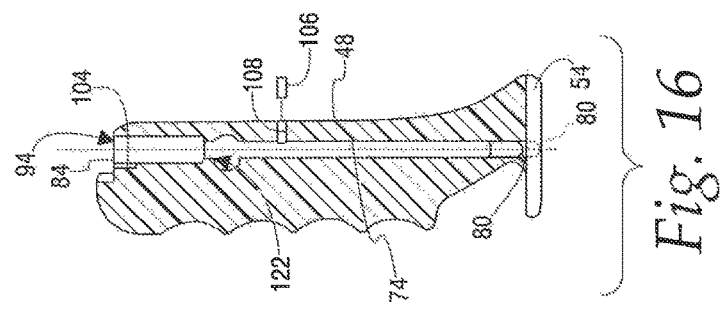
FIG. 16 is a cross-sectional view of the inserter body taken along line 16-16 of FIG. 14.
Figure 15:
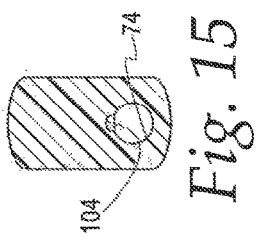
FIG. 15 is an enlarged, cross-sectional view of the inserter body taken along line 15-15 of FIG. 14.
Figure 14:
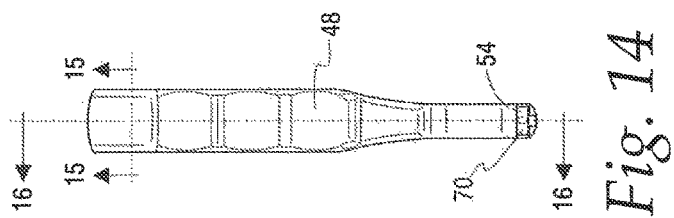
FIG. 14 is an end elevation view of the inserter body in FIG. 11.
Figure 13:
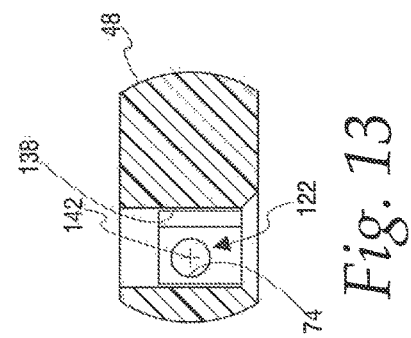
FIG. 13 is an enlarged, cross-sectional view of the inserter body taken along line 13-13 of FIG. 11.

By raising the fixing component 72 slightly from its engaged position, the locking end 80 is retracted from the slot 54, as shown in solid lines in FIG. 16, to allow the plate 12 to be withdrawn from the slot 54 or directed thereinto. This represents the released position for the fixing component 72.

The line of travel of the fixing component 72 between its engaged and released positions is transverse to the line of movement of the plate, as indicated by the double-headed arrow 66 in FIG. 8, as it is guided within the slot 54. These lines of movement are shown to be approximately orthogonal, although that is not a requirement.

To limit movement of the fixing component 72 between engaged and released positions, a post 106 is directed through the body 48 to extend into the through opening 74. As seen in FIG. 16, a bore 108 is formed and threaded to allow the externally threaded post 106 to be advanced thereinto. The post 106 moves into an annular gap 110 where the body 76 of the fixing component 72 is locally undercut. The undercut produces axially oppositely facing annular shoulders 112, 114 to which the post 106 abuts with the fixing component in the engaged and released positions, respectively.

A locking assembly is provided at 116 and includes a block 118 having a body 120 that is configured to be press fit into an operative position in a complementarily-shaped receptacle 122 on the inserter body 48. The block body 120 has actuating ends/actuators 124, 126 defined at oppositely facing surfaces. Between the actuating ends 124, 126 is a generally flat platform 128 through which an opening 130 is formed with the shape of the number "8". The opening 130 has one edge portion 132 defined by an arc with a constant radius R1 extending from a center C1. A separate edge portion 134 is defined by an arc with a smaller radius R2 extending from a center C2. The centers C1, C2 are intersected by a line L1 that is parallel to a translational path that the block 118 moves in relative to the inserter body 48, as indicated by the double-headed arrow 136.

The block 118 is assembled from an initially separated position by directing the actuating end 124 into a complementarily-shaped portion 138 of the receptacle 122. As depicted, this shape is a truncated circle. However, any cooperating arrangement that precludes turning of the block about a center line CL between the actuating ends 124, 126 is contemplated. For example, the cooperating shapes may be any polygonal shape that allows keying.

With the block 118 pressed in the direction of the arrow 140 in FIG. 12 fully into the receptacle 122, the center C2 aligns with the central axis 142 of the through opening 74. By pressing on the exposed actuating end 124 to shift the block 118 oppositely to the direction indicated by the arrow 140, the center C1 aligns with the axis 142.

The block 118 is pressed into the receptacle 122 before the fixing component 72 is directed downwardly into the through opening 74 and fully through the block opening 130. By extending through the opening 130 on the block 118, the fixing component 72 prevents the block 118 from being withdrawn from the receptacle 122.

The fixing component 72 has an annular undercut 144 producing a locally reduced diameter portion between oppositely facing, annular shoulders 146, 148. With the fixing component 72 directed downwardly into its engaged position, the full vertical thickness T1 of the platform 128 aligns with the undercut 144. By pressing the actuating end 126 with a force to move the block 118 translationally in a straight line in the direction of the arrow 150 (FIG. 18) into a first position, the central axis 152 of the fixing component 72 aligns with the center C2. The edge portion 134 wraps closely around the undercut 144 whereby the shoulder 146 abuts to the bottom 154 of the platform 128 to prevent the fixing component 72 from moving from its engaged position into its released position.

To allow the fixing component to be moved back into its released position, the opposite actuating end 124 is pressed with a force adequate to move the block 118 in the direction of the arrow 156 (FIG. 18) into a second position, which causes the fixing component axis 152 to align with the center C1. Given the larger diameter of the edge portion 132, the fixing component 72 is allowed to slide upwardly into its released position.

Selective movement of the block 118 back and forth between the aforementioned positions changes the locking assembly between locked and unlocked states. Indicia at 158, 160 gives a visual indication to a user as to which actuating end to press to select the desired state. The actuating end 126 is identified as the "lock" end whereas the actuating end 124 is identified as the "unlock" end.

A coil spring 162 normally biases the fixing component 72 towards its released position. The coil spring 162 surrounds the body 76 and abuts to an annular shoulder 164 at the bottom of the enlarged diameter portion 98 of the body 76. The coil spring 162 becomes captive between the shoulder 164 and the top 166 of the platform 128, as seen in FIG. 20. With the fixing component 72 in its engaged position, the coil spring 162 is compressed between the shoulder 164 and the platform 128. Upon repositioning the block 118 to place the locking assembly in the unlocked state, the compressed coil spring 162 biases the fixing component 72 upwardly to the released position.

While the leading plate end 24 may have a generally rounded shape viewed parallel to the planes P1, P2, as for other perimeter body regions described hereinabove, in a more preferred form, as shown in FIG. 21, the leading plate end 24" has a sharp dissecting edge at a bottom/deep surface 176 and has a superficial surface portion at 178 that tapers away from that edge towards a trailing end (not shown) so as to facilitate tissue dissection as the plate 24" is advanced, leading end first, to be operatively placed at a bone fracture site. Generally, this contour is similar to a periosteal elevator.

As the leading plate end 24" is advanced through manipulation of the inserter, dissection occurs in a plane between the bone surface and overlying soft tissue. This allows opposition of the deep surface 176, trailing the leading end 24", directly against the bone surface as the leading end 24" is advanced. The leading end 24" may have different shapes, including a curved, convex shape, as viewed orthogonally to the plane, as identified above, between the bone surface and overlying soft tissue.

By coupling the plate 12 with the inserter 14, the plate 12 is temporarily converted to function as a periosteal elevator to perform the dissection of soft tissue away from the surface of a bone. The inserter 14 functions to hold the plate 12 rigidly enough to prevent relative motion between the plate 12 and inserter 14 despite the force applied through the grasped inserter 14 as the inserter 14 is used to control the plate 12 during a procedure to perform this dissection.

Once the periosteal dissection is completed, the inserter 14 can be simply uncoupled from the plate 12, leaving the plate 12 operatively positioned at the desired location. The plate 12 can then be secured in conventional manner using well-known fasteners 18. This saves the extra step of removing an elevator and then trying to find the dissection path with the secondary plate insertion.

With the inserter body 48 grasped as shown in FIG. 9, the user's thumb situates at the location of the head 96 at the actuating end 78 of the fixing component 72. The thumb on the grasping hand can be used to press downwardly on the head 96 to thereby change the fixing component 72 from the released position into the engaged position. The actuating ends 124, 126 on the block 118 are also readily accessible to be operated through one or more digits on the grasping hand.

Figure 22:
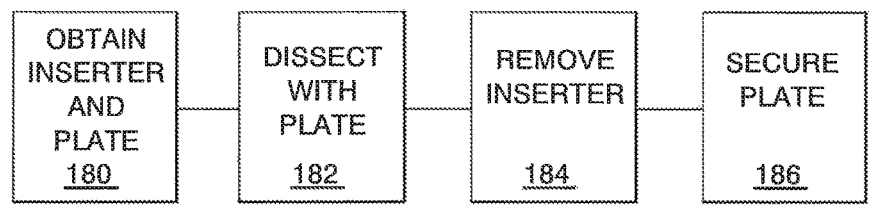
FIG. 22 is a schematic representation of a method of securing a plate to a bone at a fracture site, according to the invention.

With the exemplary system 10, as described above, a method of securing a plate to a bone at a fracture site can be performed, as shown in flow diagram form in FIG. 22.

As shown at block 180, the inserter and plate, as described hereinabove, are obtained.

With the plate operatively engaged with the inserter, the plate is manipulated through the inserter to: a) effect dissection of tissue along the desired path; and b) strategically place the plate against bone at the fracture site, as indicated at block 182.

As shown at block 184, the inserter can be removed/separated from the plate, either before or after securement of the plate to the bone.

As indicated at block 186, the plate is secured to the bone in conventional fashion.

Figure 23:
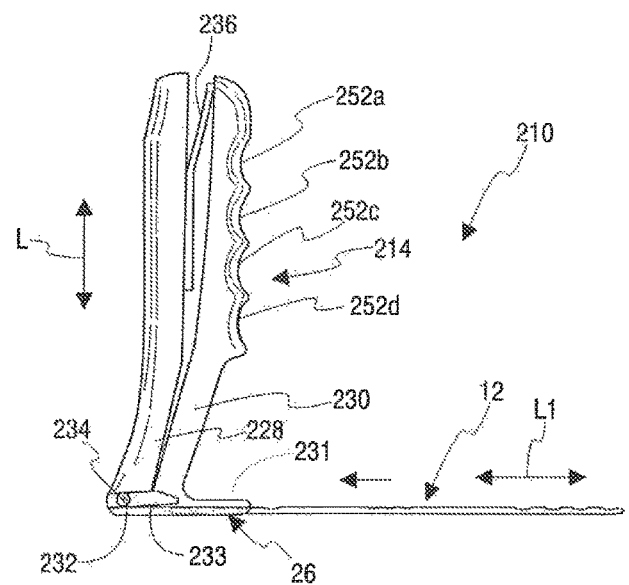
FIG. 23 is a side elevation view of another form of assembly, according to the invention, including a modified form of inserter cooperating with a plate, as shown in FIG. 3, and with the inserter in a state that allows the plate to be selectively operatively engaged by the inserter and released therefrom.
Figure 24:
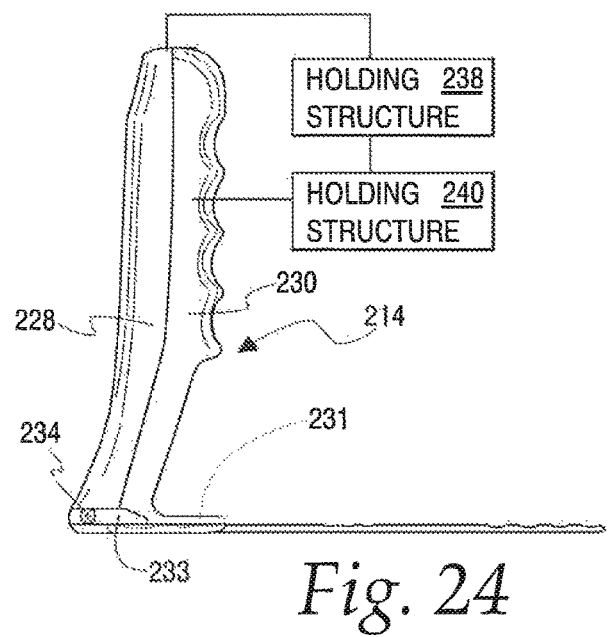
FIG. 24 is a view as in FIG. 23 wherein the inserter is reconfigured to maintain the plate on the inserter.

Another exemplary form of the inventive system is shown at 210 in FIGS. 23 and 24.

An inserter 214 has vertically elongate grip parts 228, 230 that are connected, at adjacent ends thereof, by a pin 232 that guides the grip parts 228, 230 in relative movement around an axis 234 between a holding relationship, shown in FIG. 24, and a released relationship, as shown in FIG. 23. A spring plate 236 acts between the grip parts 228, 230 to normally urge the grip part 228 in a counterclockwise direction around the axis 234 and relative to the grip part 230 wherein the fixed grip parts are in the released relationship of FIG. 23.

In this embodiment, the grip part 230 defines a slot/track 231 into which the plate part/trailing end 26 is directed, as by translation generally as occurs with the earlier described embodiment. In one form, the slot/track 231, trailing end 26 of the plate 12, and grip parts 228, 230 are configured so that as the grip parts 228, 230 are changed from their released relationship into their holding relationship, by squeezing the grip parts 228, 230 together, a foot/fixing component 233 on the grip part 228, initially in a released position, pivots/translates downwardly into an engaged position wherein the foot/fixing component 233 wedges the plate trailing end 26 in the slot/track 231.

Cooperating holding structure 238, 240 may be provided on the grip parts 228, 230, respectively, to releasably maintain the grip parts 228, 230 in the holding relationship. Alternatively, the holding relationship may be maintained only by a grasping pressure applied by the user, whereby grip pressure release frees the plate 12 from the inserter 214.

The grip part 230 has a series of receptacles 252$a$, 252$b$, 252$c$, 252$d$ into which the user's fingers can be placed to allow the grip part 230 to be urged against the grip part 228, with the latter braced against the user's palm region. With this arrangement, the inserter 214 is ergonomically configured to comfortably be held by the surgeon without the need for excessive grip power. In addition, with this embodiment, as with the earlier described embodiment, the generally right angle relationship between the vertical length of the grip parts 228, 230 on the inserter 214, indicated by the double-headed arrow L, and the length of the plate 12, indicated by the double-headed arrow L1, provides the necessary functional clearance with limbs/bones during dissection.

Figure 25:
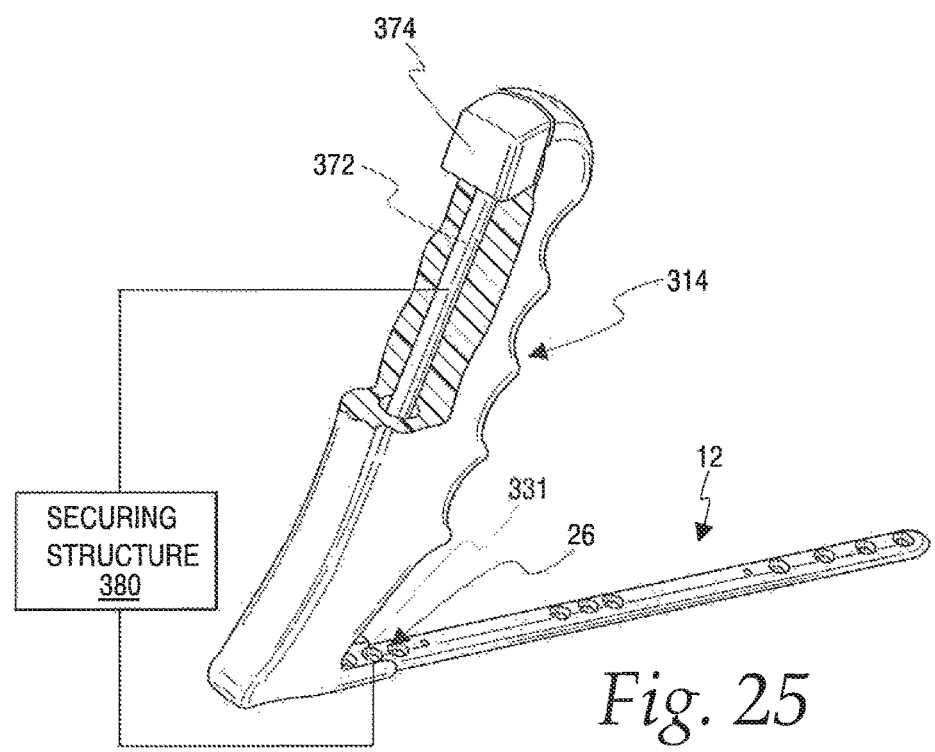
FIG. 25 is a perspective view of a further modified form of inserter, partially broken away and with another mechanism for maintaining a plate, as in FIG. 3, operatively engaged with the inserter.

The design of the inserter may have still further numerous variations. For example, the plate end 26, shown in FIG. 25, can slide within a slot/track 331 at the lower end of the inserter 314. It can be held by a fastener 372 that extends into the plate 12. Alternatively, or additionally, the plate 12 can be held in the inserter slot/track 331 by simply bearing the fastener 372 against the seated plate 12. The fastener; while not so limited in construction, is shown as a bar 372 running vertically through the inserter body that can be pressed against the plate 12 or directed through one of the fastener openings therein using the thumb of the hand grasping the inserter 314 to apply downward pressure to an upper actuating head 374. Securing structure 380 may releasably maintain the bar 372 in its downward position.

Alternatively, a cam mechanism could be used to press against a surface of the plate 12 in the slot/track. Other variations are contemplated within the generic showing of the invention in FIG. 1.

Common to many anticipated forms, within the generic showing herein, is an inserter construction capable of being placed in first and different states. In a first state for the inserter, the plate can be translated in at least one line into and out of a slot/receptacle defined on the inserter for the plate to thereby be respectively operatively positioned and separated from the inserter. The inserter can be changed into a second state to be securely coupled/engaged with the operatively positioned plate.

As one additional example, a variable length plate 12 is contemplated within the generic showing in FIGS. 1 and 2 which can be controlled by a distracting or compressing instrument 400. A suitable instrument for that purpose is shown in U.S. Pat. No. 9,220,546, the disclosure of which is incorporated herein by reference.

The foregoing disclosure of specific embodiments is intended to be illustrative of the broad concepts comprehended by the invention.

The invention claimed is:

1. In combination:
    a) a plate configured to be operatively placed at a bone fracture site and secured with at least one fastener to stabilize bone portions between which a fracture is located,
    the plate having a tapered leading end; and
    b) an inserter,
    there being structure cooperating between the plate and inserter configured to releasably maintain the plate operatively engaged with the inserter,
    the operatively engaged plate movable together with the inserter whereby a user can reorient and advance the operatively engaged plate through the inserter,
    wherein with the plate operatively engaged with the inserter, the plate and inserter are configured so that by manipulating the inserter the tapered leading end can be advanced to dissect soft tissue along a bone surface to allow a surface portion on the plate that trails the leading end, as the leading end is advanced, to be operatively placed against the bone surface across the bone fracture site,
    wherein the inserter has a top and bottom, and comprises a body, and the structure cooperating between the plate and inserter comprises a slot on the body in which a part of the plate resides with the plate operatively engaged,
    wherein the structure cooperating between the plate and inserter comprises a fixing component that is movable guidingly in translation relative to the body between engaged and released positions, the plate part movable into and out of the slot with the fixing component in the released position and maintained in the slot with the fixing component in the engaged position.

2. The combination according to claim 1 wherein the inserter is configured to be changed between a first state, wherein the fixing component is in the released position and the plate may translate in at least one line to be selectively: a) operatively positioned in a receptacle on the inserter; and b) separated from the inserter, and a second state, wherein the fixing component is in the engaged position and the operatively positioned plate is engaged/coupled with the inserter.

3. The combination according to claim 1 wherein the inserter body has a vertically elongate shape with an exterior surface configured to be grasped between a user's palm and a plurality of a user's fingers.

4. The combination according to claim 3 wherein the vertically elongate shape has an axis, the plate has a lengthwise axis, and the axis of the vertically elongate shape is at an angle of at least 45 degrees to the lengthwise axis of the plate with the plate operatively engaged with the inserter.

5. The combination according to claim 3 wherein the body has a plurality of vertically spaced, discrete receptacles each for a user's finger.

6. The combination according to claim 1 wherein the body and the part of the plate are configured so that the part of the plate is movable into and out of the slot by relatively translating the body and the part of the plate along a first line.

7. The combination according to claim 6 wherein the first line is horizontally oriented relative to the body.

8. The combination according to claim 1 wherein the body and the part of the plate are configured so that the part of the plate is movable into and out of the slot by relatively translating the body and the part of the plate along a first line and the fixing component is movable between the engaged and released positions along a second line that is transverse to the first line.

9. The combination according to claim 1 wherein the plate has an opening and the fixing component has a free end that extends into the opening with the fixing component in the engaged position.

10. The combination according to claim 9 wherein the opening is configured to accept a fastener configured to be directed through the opening and into a bone to secure the operatively placed plate.

11. The combination according to claim 1 further in combination with a plurality of fasteners configured to fix the plate to bone at the bone fracture site.

12. The combination according to claim 1 wherein the plate has an elongate body with a length and a thickness between first and second oppositely facing surfaces, the surface portion on the plate that trails the leading end, as the leading end is advanced, is a part of one of the first and second oppositely facing surfaces, and the plate has a plurality of fastener openings each extending through the body and the first and second surfaces.

13. The combination according to claim 12 wherein the first and second surfaces are substantially flat over a substantial length of the plate body to reside in first and second substantially parallel planes.

14. The combination according to claim 12 wherein a length of one of the first and second surfaces is twisted out of the first plane to conform to bone at a human ankle region.

15. The combination according to claim 12 wherein the plate body has a truncated tubular shape over a substantial length of the plate body.

16. The combination according to claim 15 wherein the inserter further comprises a locking assembly changeable between locked and unlocked states, with the fixing component in the engaged position and the locking assembly in the locked state, the fixing component is blocked from moving into the released position, and with the locking assembly in the unlocked state the fixing component can be moved between the engaged and released positions.

17. The combination according to claim 1 wherein the leading end of the plate has a sharp dissecting edge and tapers away from the dissecting edge towards a trailing end of the plate to facilitate tissue dissection as the plate is advanced leading end first to be operatively placed at the bone fracture site.

18. The combination according to claim 17 wherein the sharp dissecting edge is situated on a deep surface of the plate and the taper is located at a superficial surface of the plate so as to facilitate dissection in a plane between the bone surface and overlying soft tissue and apposition of the deep surface directly against the bone surface as the leading end is advanced through manipulation of the inserter.

19. The combination according to claim 18 wherein the leading end has a curved, convex shape as viewed orthogonally to the plane between the bone surface and overlying soft tissue.

20. The combination according to claim 1 wherein the fixing component is guided in translation in a substantially linear path between the engaged and released positions.

21. In combination:
a) a plate configured to be operatively placed at a bone fracture site and secured with at least one fastener to stabilize bone portions between which a fracture is located,
the plate having a tapered leading end; and
b) an inserter,
there being structure cooperating between the plate and inserter configured to releasably maintain the plate operatively engaged with the inserter,
the operatively engaged plate movable together with the inserter whereby a user can reorient and advance the operatively engaged plate through the inserter,
wherein with the plate operatively engaged with the inserter, the plate and inserter are configured so that by manipulating the inserter the tapered leading end can be advanced to dissect soft tissue along a bone surface to allow a surface portion on the plate that trails the advancing leading end to be operatively placed against the bone surface across the bone fracture site,
wherein the inserter has a top and bottom, the inserter comprises a body, and the structure cooperating between the plate and inserter comprises a slot on the body in which a part of the plate resides with the plate operatively engaged,
wherein the structure cooperating between the plate and inserter comprises a fixing component that is movable guidingly relative to the body between engaged and released positions, the plate part movable into and out of the slot with the fixing component in the released position and maintained in the slot with the fixing component in the engaged position,
wherein the fixing component is normally biased towards the released position.

22. The combination according to claim 21 further comprising a locking assembly having locked and unlocked states, the locking assembly configured so that in the locked state the fixing component is maintained in the engaged position, the locking assembly configured so that in the unlocked state the fixing component can move between the engaged and released positions.

23. The combination according to claim 22 wherein the locking assembly comprises a block that is movable guidingly relative to the body between first and second positions, the locking assembly in the locked state with the block in the first position, the locking assembly in the unlocked state with the block in the second position.

24. The combination according to claim 23 wherein the block is movable in a substantially straight line between the first and second positions, the body has oppositely facing first and second surfaces and the locking assembly comprises first and second actuators, respectively at the first and second surfaces, that are engageable by a user to selectively move the block between the first and second positions.

25. The combination according to claim 21 wherein with the inserter separated from the plate, the fixing component is normally biased into the released position.

26. A method of securing a plate to a bone at a fracture site, the method comprising the steps of:
obtaining the combination of claim 1,
wherein with the plate operatively engaged with the inserter, the plate extends in cantilever fashion such that the leading end of the plate is unsupported by the inserter,
wherein the plate has an opening and the fixing component has a free end that extends into the opening with the fixing component in the engaged position;
with the plate operatively engaged with the inserter, manipulating the inserter to: a) cause the plate to dissect tissue at the fracture site; and b) operatively place the plate at a desired location at the fracture site;
separating the inserter from the plate; and
securing the operatively placed plate to bone at the fracture site,
wherein the step of securing the operatively placed plate to bone comprises directing a fastener through the opening and into the bone.

27. In combination:
a) a plate configured to be operatively placed at a bone fracture site and secured with at least one fastener to stabilize bone portions between which a fracture is located,
the plate having a tapered leading end; and
b) an inserter,
there being structure cooperating between the plate and inserter configured to releasably maintain the plate operatively engaged with the inserter,
the operatively engaged plate movable together with the inserter whereby a user can reorient and advance the operatively engaged plate through the inserter,
wherein with the plate operatively engaged with the inserter, the plate and inserter are configured so that by manipulating the inserter the tapered leading end can be advanced to dissect soft tissue along a bone surface to allow a surface portion on the plate that trails the leading end, as the leading end is advanced, to be operatively placed against the bone surface across the bone fracture site,
wherein the inserter has a top and bottom, and comprises a body, and the structure cooperating between the plate and inserter comprises a slot on the body in which a part of the plate resides with the plate operatively engaged, wherein the structure cooperating between the plate and inserter comprises a fixing component that is movable guidingly relative to the body between engaged and released positions, the plate part movable into and out of the slot with the fixing component in the released position and maintained in the slot with the fixing component in the engaged position, wherein the fixing component is normally biased by a spring into one position.

28. In combination:
a) a plate configured to be operatively placed at a bone fracture site and secured with at least one fastener to stabilize bone portions between which a fracture is located,
the plate having a tapered leading end; and
b) an inserter,
there being structure cooperating between the plate and inserter configured to releasably maintain the plate operatively engaged with the inserter,
the operatively engaged plate movable together with the inserter whereby a user can reorient and advance the operatively engaged plate through the inserter,
wherein with the plate operatively engaged with the inserter, the plate and inserter are configured so that by manipulating the inserter the tapered leading end can be advanced to dissect soft tissue along a bone surface to allow a surface portion on the plate that trails the leading end, as the leading end is advanced, to be operatively placed against the bone surface across the bone fracture site,
wherein the inserter has a top and bottom, and comprises a body, and the structure cooperating between the plate and inserter comprises a slot on the body in which a part of the plate resides with the plate operatively engaged,
wherein the structure cooperating between the plate and inserter comprises a fixing component that is movable guidingly in translation relative to the body between engaged and released positions, the plate part movable into and out of the slot with the fixing component in the released position and maintained in the slot with the fixing component in the engaged position.

29. In combination:
a) a plate configured to be operatively placed at a bone fracture site and secured with at least one fastener to stabilize bone portions between which a fracture is located,
the plate having a tapered leading end; and
b) an inserter,
there being structure cooperating between the plate and inserter configured to releasably maintain the plate operatively engaged with the inserter,
the operatively engaged plate movable together with the inserter whereby a user can reorient and advance the operatively engaged plate through the inserter,
wherein with the plate operatively engaged with the inserter, the plate and inserter are configured so that by manipulating the inserter the tapered leading end can be advanced to dissect soft tissue along a bone surface to allow a surface portion on the plate that trails the leading end, as the leading end is advanced, to be operatively placed against the bone surface across the bone fracture site,
wherein the inserter has a top and bottom, and comprises a body, and the structure cooperating between the plate and inserter comprises a slot on the body in which a part of the plate resides with the plate operatively engaged,
wherein the structure cooperating between the plate and inserter comprises a fixing component that is movable guidingly in translation in a predetermined path between engaged and released positions, the plate part movable into and out of the slot with the fixing component in the released position and maintained in the slot with the fixing component in the engaged position.

30. In combination:
a) a plate configured to be operatively placed at a bone fracture site and secured with at least one fastener to stabilize bone portions between which a fracture is located,
the plate having a length between a trailing end and a tapered leading end; and
b) an inserter,
there being structure cooperating between the plate and inserter configured to releasably maintain the plate operatively engaged with the inserter,
the operatively engaged plate movable together with the inserter whereby a user can reorient and advance the operatively engaged plate through the inserter,
wherein with the plate operatively engaged with the inserter, the plate and inserter are configured so that by manipulating the inserter the tapered leading end can be advanced to dissect soft tissue along a bone surface to allow a surface portion on the plate that trails the leading end, as the leading end is advanced, to be operatively placed against the bone surface across the bone fracture site,
wherein the structure cooperating between the plate and inserter comprises a slot on the body, with a width and a height, in which a part of the body resides with the plate operatively engaged,
wherein the plate has a width approximately equal to the width of the slot over a majority of the length of the plate,
wherein with the plate operatively engaged by the inserter, the plate extends in cantilever fashion from the inserter such that the tapered leading end of the plate is unsupported by the inserter.

* * * * *